United States Patent [19]

Kummer et al.

[11] 4,316,047

[45] Feb. 16, 1982

[54] PREPARATION OF $C_1$-$C_4$-ALKYL PENT-3-ENOATES

[75] Inventors: Rudolf Kummer, Frankenthal; Franz-Josef Weiss, Weinheim; Heinz-Walter Schneider; Volker Taglieber, both of Ludwigshafen, all of Fed. Rep. of Germany

[73] Assignee: BASF Aktiengesellschaft, Fed. Rep. of Germany

[21] Appl. No.: 166,569

[22] Filed: Jul. 7, 1980

[30] Foreign Application Priority Data

Aug. 18, 1979 [DE] Fed. Rep. of Germany ....... 2933581

[51] Int. Cl.³ .............................................. C07C 67/38
[52] U.S. Cl. .................................................... 560/206
[58] Field of Search ........................ 560/206; 562/533

[56] References Cited

U.S. PATENT DOCUMENTS 3,778,466 12/1973 Matsuda .............................. 560/206

FOREIGN PATENT DOCUMENTS 2630086 12/1978 Fed. Rep. of Germany .

Primary Examiner—Natalie Trousof
Assistant Examiner—L. Hendriksen
Attorney, Agent, or Firm—Keil & Witherspoon

[57] ABSTRACT

A process for the preparation of $C_1$-$C_4$-alkyl pent-3-enoates, wherein butadiene, or a hydrocarbon mixture containing butadiene, either of which contains not more than 0.1% by weight of butynes, is reacted with carbon monoxide and an alkanol of 1 to 4 carbon atoms in the presence of a cobalt carbonyl catalyst and a tertiary nitrogen base, having a $pK_A$ of 3-11, at from 100° to 140° C. under a pressure of from 300 to 1,000 bar.

3 Claims, No Drawings

PREPARATION OF $C_1$–$C_4$-ALKYL PENT-3-ENOATES

The present invention relates to a process for the preparation of $C_1$–$C_4$-alkyl pent-3-enoates wherein butadiene, or a hydrocarbon mixture containing butadiene, is reacted with carbon monoxide and an alkanol of 1 to 4 carbon atoms in the presence of a cobalt catalyst and a tertiary nitrogen base, having a $pK_A$ of 3–11, at from 100° to 140° C. under a pressure of from 300 to 1,000 bar.

German Laid-Open Application DOS No. 2,630,086 describes a process for the preparation of pent-3-enoic acid esters by carbonylation of butadiene or of a hydrocarbon mixture containing butadiene. Though the process gives good yields, it is not entirely satisfactory since substantial amounts of high-boiling materials are formed, and this also reduces the selectivity in respect of the formation of the alkyl pent-3-enoate.

It is an object of the present invention to carry out the preparation of alkyl pent-3-enoates, by carbonylation of butadiene or of a hydrocarbon mixture containing butadiene, in such a way that the proportion of high-boiling products is reduced and the selectivity in respect of formation of the desired product is increased.

We have found that this object is achieved by a process for the preparation of $C_1$–$C_4$-alkyl pent-3-enoates wherein butadiene, or a hydrocarbon mixture containing butadiene, is reacted with carbon monoxide and an alkanol of 1 to 4 carbon atoms in the presence of a cobalt carbonyl catalyst and a tertiary nitrogen base, having a $pK_A$ of 3–11, at from 100° to 140° C. under a pressure of from 300 to 1,000 bar, the content of butynes in the butadiene used, or in the butadiene-containing hydrocarbon mixture used, being not more than 0.1% by weight.

The novel process has the advantage that the formation of high-boiling products is substantially reduced and at the same time the selectivity in respect of the formation of alkyl pent-3-enoates is increased. It has in fact been found that butynes, in particular vinylacetylene, which are present in technical-grade butadiene or in hydrocarbon mixtures containing butadiene, and which may constitute up to 3% by weight, have an adverse effect on the carbonylation. Vinylacetylene has the further disadvantageous effect that under the reaction conditions used it reacts with butadiene to form butenedicarboxylic acid diesters, vinylpropionic acid esters, cinnamic acid esters, phenylacetylenecarboxylic acid esters and other high-boiling carboxylation products. This results in additional consumption of butadiene, to form high-boiling products.

The novel process employs 1,3-butadiene or butadiene-containing hydrocarbon mixtures. Such hydrocarbon mixtures for example contain, in addition to butadiene, saturated hydrocarbons of 3 to 5 carbon atoms and monoolefinically unsaturated hydrocarbons of 3 to 5 carbon atoms. The butadiene content should as a rule be greater than 10% by weight. In industry, $C_4$-cuts, in particular, are used as starting mixtures. For the purposes of the invention, such mixtures are all those which predominantly consist of non-branched $C_4$-hydrocarbons and which contain more than 10% by weight of 1,3-butadiene. Such mixtures may have the following compositions, the exact amount of the individual components depending on the origin of the mixture: 40–60% by weight of butadiene, 20–35% by weight of isobutene, 10–25% by weight of but-1-ene, 5–15% by weight of but-2-ene and 1–10% by weight of butanes. Such $C_4$-cuts are obtained, for example, from the dehydrogenation of butane or butene or as a by-product of the production of ethylene by thermal cracking of light gasoline or of higher hydrocarbon cuts.

It is an essential feature of the invention that the above starting materials contain not more than 0.1% by weight of butynes and in particular that they do not contain more than 0.05% by weight of vinylacetylene. These percentages are each based on the total mixture of the butadiene employed or of the butadiene-containing hydrocarbon mixture.

Butadiene, or butadiene-containing hydrocarbon mixtures, conforming to the requirements of the invention in respect of the butyne content are advantageously obtained by partial hydrogenation of the butadiene or butadiene-containing hydrocarbon mixture with hydrogen at from 20° to 60° C. under a pressure of from 1 to 50 bar, in the presence of a noble metal catalyst, especially palladium. $C_4$-cuts partially hydrogenated in this way are particularly preferred as the starting material.

Examples of suitable alkanols are methanol, ethanol, propanol and butanol, amongst which methanol is particularly preferred. It has proved advantageous to employ the alkanols in excess and in particular to use from 1 to 5 moles of alkanol per mole of butadiene.

The reaction is preferably carried out at from 120° to 140° C. under a pressure of from 600 to 1,000 bar. As a rule, from 0.05 to 0.15 gram atom of cobalt, in the form of a cobalt carbonyl complex, eg. cobalt tetracarbonyl or cobalt octacarbonyl, is used per mole of butadiene. Carbon monoxide is advantageously used in excess, for example in from 1.5 to 10 times the stoichiometric amount.

Examples of suitable tertiary nitrogen bases having a $pK_A$ of from 3 to 11 are pyridine, methylpyridines, isoquinoline and trialkylamines, eg. trimethylamine and triethylamine. The use of N-heterocyclic compounds, eg. pyridine, methylpyridines or isoquinoline is however particularly advantageous; industrially, pyridine is of special importance for this purpose. It has proved particularly advantageous to use from 5 to 50 moles of nitrogen base, eg. pyridine, per mole of cobalt carbonyl catalyst.

Advantageously, the cobalt catalyst used is introduced into the reaction mixture as previously prepared cobalt carbonyl, in particular as a solution thereof in butadiene or in the $C_4$-cut. Such a solution is obtained, for example, by reacting an aqueous solution of a fatty acid salt of cobalt, eg. the acetate or butyrate, with a mixture of carbon monoxide and hydrogen in the presence of active charcoal at from 100° to 170° C. under a pressure of from 100 to 400 bar, and then extracting the resulting cobalt carbonyl from the aqueous solution with butadiene or with a $C_4$-cut.

The mixture resulting after reaction contains unconverted butadiene (with or without other hydrocarbons), tertiary nitrogen base, the cobalt carbonyl catalyst, excess alkanol, the alkyl pent-3-enoate constituting the intended product, and by-products such as valeric acid esters, butadiene polymers and high-boiling compounds.

The alkyl pent-3-enoates obtained according to the invention may be isolated by distillation and then used to prepare dialkyl butanedicarboxylates by carbonylation. It is also possible to use the reaction mixture obtained directly, without removing the catalyst, for further carbonylation to give dialkyl butanedicarboxylates.

The Examples which follow illustrate the process according to the invention.

COMPARATIVE EXAMPLE 1

A mixture of 54 g (1.0 mole) of 1,3-butadiene, 2.7 g (0.05 mole) of vinylacetylene, corresponding to 5% by weight based on butadiene, 79.1 g (1.0 mole) of pyridine, 38.5 g (1.2 moles) of methanol and 0.04 gram atom of cobalt in the form of dicobalt octacarbonyl is pumped into a high pressure vessel of 0.5 liter capacity. The carbonylation reaction is carried out at 135° C. and 900 bar for 110 minutes with replenishment of the carbon monoxide, until the absorption of gas ceases. The amount of residue left after distillation is 14.5% by weight (after deducting the catalyst dissolved in the residue), based on pentenoic acid ester produced, whilst analysis of the distillate by gas chromatography shows the yield of methyl pent-3-enoate to be 78%, based on butadiene employed.

EXAMPLE 1

Comparative Example 1 is repeated, except that the butadiene employed has been virtually completely freed from vinylacetylene by hydrogenation (the vinylacetylene content being <0.1 mole %). The content of butynes is 0.1% by weight. The amount of residue produced is in this reaction only 3.5% by weight, based on pentenoic acid ester, and the yield of the latter is 92%.

COMPARATIVE EXAMPLE 2

An autoclave of 2.3 liters capacity is operated continuously, being fed per hour with 405 g of a C4-cut, containing 162 g (3 moles) of butadiene and 3.2 g (0.06 mole) of vinylacetylene (corresponding to 0.8% by weight, based on the C4-cut), 237 g (3 moles) of pyridine, 115.2 g (3.6 moles) of methanol, 168 g (6 moles) of carbon monoxide and 1.2 gram atom of cobalt in the form of cobalt carbonyl. The carbonylation reaction is carried out at 135° C. and 900 bar. Per hour, 653 g of liquid phase are discharged from the autoclave. The amount of residue formed is determined by distillation and is found to be 10% by weight, based on methyl pentenoate produced. This 10% contains 2% of dimethyl adipate, so that effectively 8% by weight of valueless high-boiling products are formed. The yield of methyl pentenoate, determined by gas chromatographic analysis, is 88%, based on butadiene employed.

EXAMPLE 2

Comparative Example 2 is repeated. However, 405 g of a C4-cut containing 165 g (3.06 moles) of butadiene and 0.05% by weight of vinylacetylene, based on the C4-cut, are employed. Per hour, 644 g of liquid reaction mixture are discharged. The amount of residue, determined by distillation, is in this case 6% by weight, based on methyl pentenoate, of which, again, 2% is dimethyl adipate, so that only 4% by weight of valueless high-boiling products are formed. The yield, determined by gas chromatography, is 93% based on butadiene employed.

We claim:

1. A process for producing $C_1$–$C_4$-alkyl pent-3-enoates which comprises: partially hydrogenating a butadiene-containing hydrocarbon mixture containing more than 0.1% by weight of butynes to reduce the butyne content of the mixture to 0.1% or less by weight and thereafter reacting the so treated mixture with carbon monoxide and an alkanol of 1 to 4 carbon atoms in the presence of a cobalt carbonyl catalyst and a tertiary nitrogen base having a $pK_A$ of from 3 to 11, at 100°–140° C. and under a pressure of from 300 to 1,000 bar.

2. The process of claim 1, wherein the vinylacetylene content butadiene-containing mixture employed is not more than 0.05% by weight.

3. The process of claim 2 or 1, wherein a C4-cut is used which has been treated with hydrogen at from 20° to 60° C. under a pressure of from 1 to 50 bar in the presence of a noble metal catalyst.

* * * * *